US012616409B2

(12) United States Patent
Ghosalker et al.

(10) Patent No.: US 12,616,409 B2
(45) Date of Patent: May 5, 2026

(54) THREE-DIMENSIONAL DISPLAY OF A MULTI-ELECTRODE CATHETER AND SIGNALS ACQUIRED OVER TIME

(71) Applicant: BIOSENSE WEBSTER (ISRAEL) LTD., Yokneam (IL)

(72) Inventors: Daniel Ghosalker, Yokneam Ilit (IL); Meytal Segev, Haifa (IL); Nir Yanovich, Binyamina-Giv'at Ada (IL); Roy Haim Karny, Kfar Glikson (IL); Alon Ben Natan, Kiryat Bialik (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 705 days.

(21) Appl. No.: 17/992,089

(22) Filed: Nov. 22, 2022

(65) Prior Publication Data

US 2024/0164686 A1     May 23, 2024

(51) Int. Cl.
*A61B 5/318* (2021.01)
*A61B 5/287* (2021.01)

(52) U.S. Cl.
CPC .............. *A61B 5/318* (2021.01); *A61B 5/287* (2021.01)

(58) Field of Classification Search
None
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben |
| 5,558,091 A | 9/1996 | Acker |
| 6,172,499 B1 | 1/2001 | Ashe |
| 6,239,724 B1 | 5/2001 | Doron |
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben |
| 6,788,967 B2 | 9/2004 | Ben |
| 6,892,091 B1 | 5/2005 | Ben |
| 7,536,218 B2 | 5/2009 | Govari et al. |
| 7,596,406 B2 | 9/2009 | Boese |
| 7,756,576 B2 | 7/2010 | Levin |
| 7,848,787 B2 | 12/2010 | Osadchy |
| 7,869,865 B2 | 1/2011 | Govari et al. |
| 8,456,182 B2 | 6/2013 | Bar-Tal et al. |

(Continued)

FOREIGN PATENT DOCUMENTS

EP          2689722 B1     6/2017

OTHER PUBLICATIONS

International Search Report for Corresponding PCT Appln. No. PCT/IB2023/061474 dated Mar. 25, 2024.

*Primary Examiner* — Yi-Shan Yang

(57) ABSTRACT

A system includes an interface and a processor. The interface is configured to receive, from at least first and second electrodes of a catheter, first and second signals, respectively, which are acquired over at least a time interval by the at least first and second electrodes at an organ of a patient. The processor is configured to produce a three-dimensional (3D) representation of at least a portion of the catheter and first and second traces corresponding to the first and second signals, and the first and second traces are displayed in a 3D space relative to physical positions of the first and second electrodes on the catheter, respectively.

14 Claims, 2 Drawing Sheets

(56) References Cited

U.S. PATENT DOCUMENTS

| | | | |
|---|---|---|---|
| 10,542,888 B2 | 1/2020 | Zeidan | |
| 11,160,485 B2 | 11/2021 | Botzer | |
| 2003/0036696 A1* | 2/2003 | Willis | A61B 5/287 |
| | | | 600/424 |
| 2006/0241518 A1* | 10/2006 | Boese | A61B 5/339 |
| | | | 600/585 |
| 2018/0070844 A1 | 3/2018 | Ashihara | |
| 2018/0296111 A1* | 10/2018 | Deno | A61B 5/746 |
| 2019/0365271 A1* | 12/2019 | Ghosh | A61N 1/37211 |
| 2021/0228139 A1 | 7/2021 | Rubenstein | |
| 2022/0192735 A1 | 6/2022 | Govari | |
| 2022/0211314 A1 | 7/2022 | Govari | |

* cited by examiner

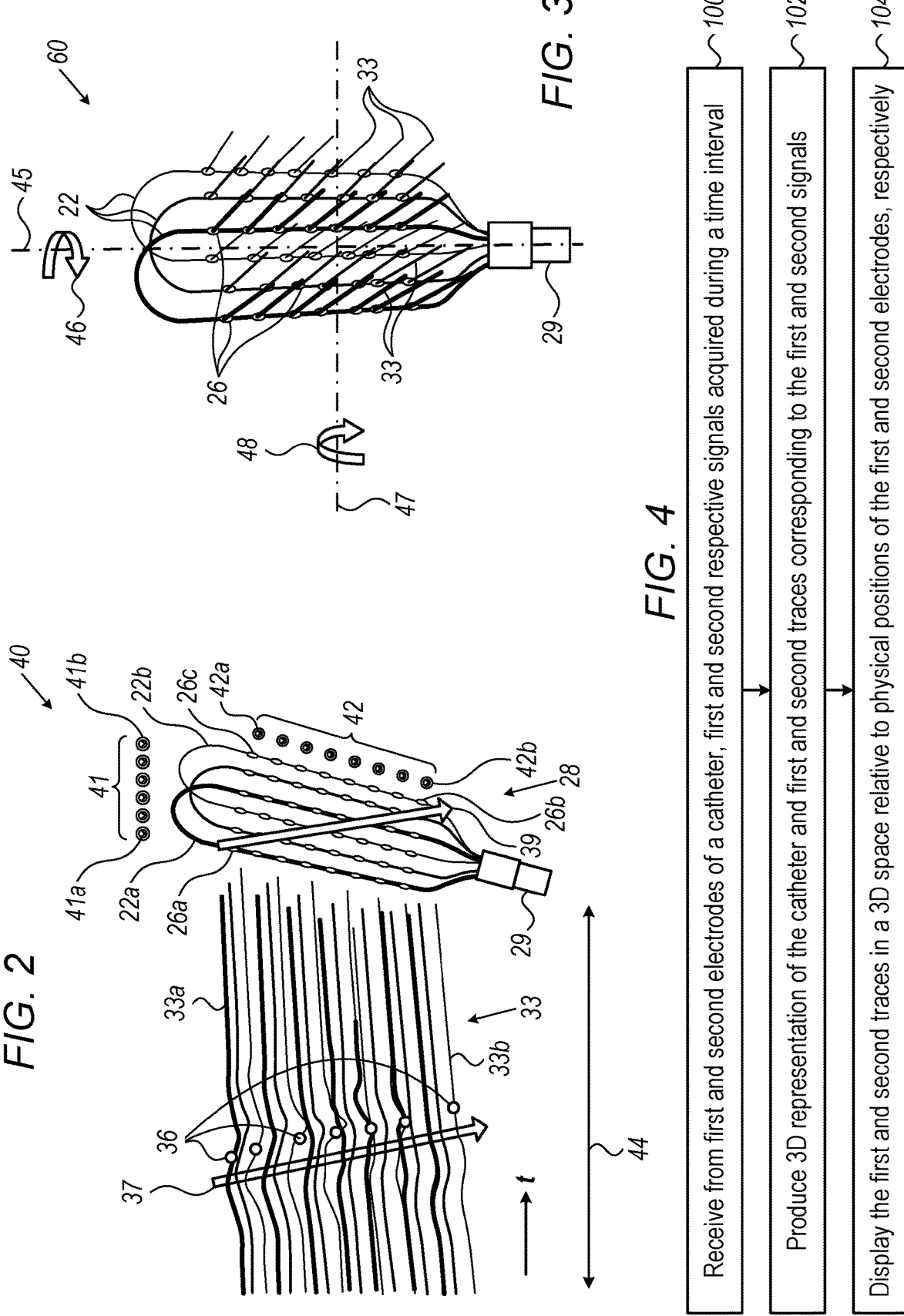

100 Receive from first and second electrodes of a catheter, first and second respective signals acquired during a time interval 102 Produce 3D representation of the catheter and first and second traces corresponding to the first and second signals 104 Display the first and second traces in a 3D space relative to physical positions of the first and second electrodes, respectively

THREE-DIMENSIONAL DISPLAY OF A MULTI-ELECTRODE CATHETER AND SIGNALS ACQUIRED OVER TIME

FIELD OF THE DISCLOSURE

The present disclosure relates generally to medical devices, and particularly to methods and systems for improving the presentation and visualization of signals acquired by multi-electrode catheters.

BACKGROUND OF THE DISCLOSURE

Various techniques for presenting electro-anatomical (EA) signals have been published. One of the challenges is to visualize the signals that are acquired over time using catheters having many electrodes.

The present disclosure will be more fully understood from the following detailed description of the examples thereof, taken together with the drawings in which:

BRIEF DESCRIPTION OF THE DRAWINGS

FIGS. 2 and 3 are schematic, pictorial illustrations of a multi-electrode catheter and EA signals acquired over time, in accordance with examples of the present disclosure; and FIG. 4 is a flow chart that schematically illustrates a method for displaying at least a portion of the catheter of FIG. 2 and signals acquired by the electrodes over time, in accordance with an example of the present disclosure.

DETAILED DESCRIPTION OF EXAMPLES

Overview

Figure 1:
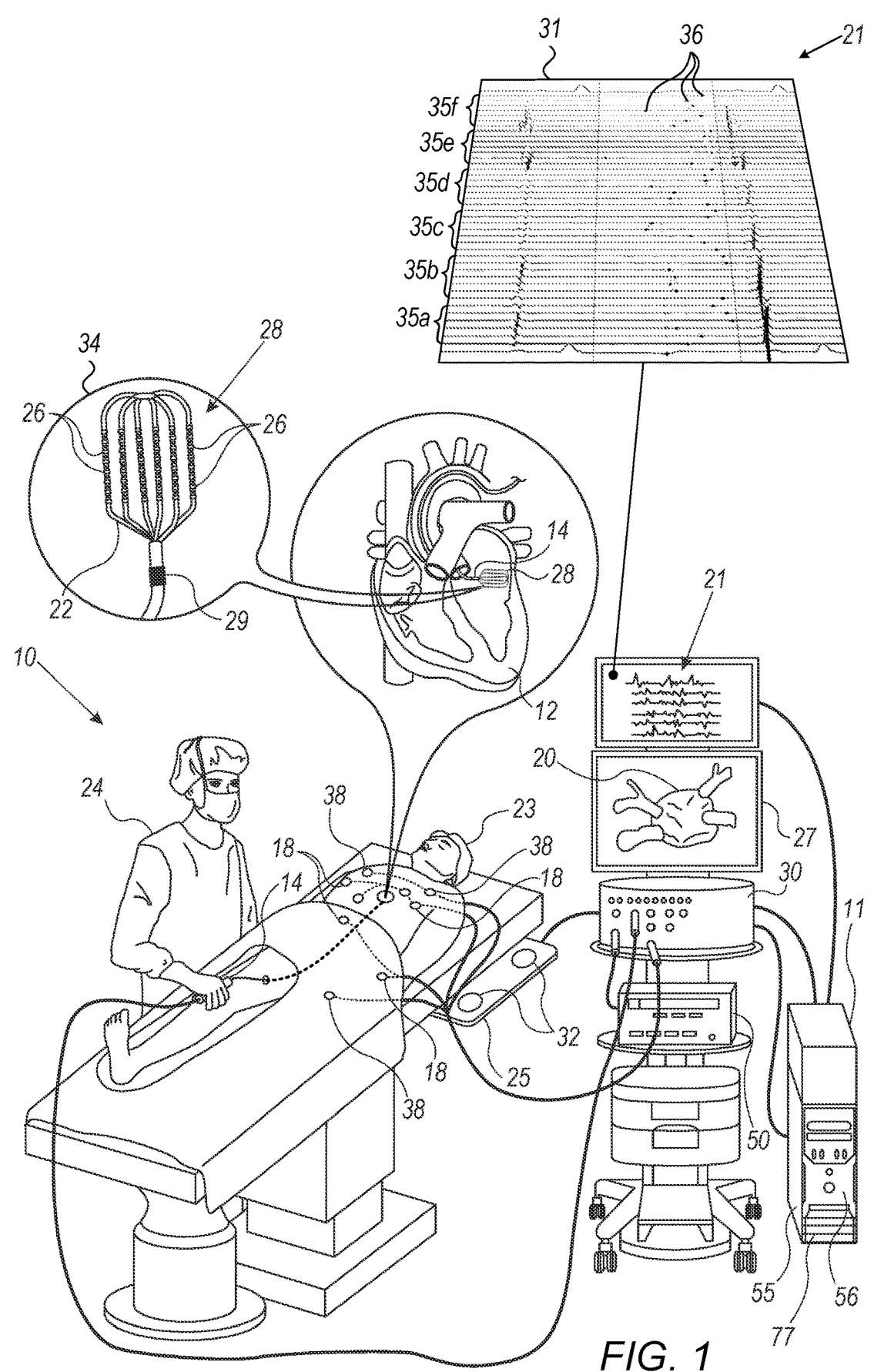
FIG. 1 is a schematic, pictorial illustration of a catheter-based electrophysiology mapping and ablation system, in accordance with an example of the present disclosure.

Examples of the present disclosure that are described below, provide techniques for improving the presentation of multiple signals acquired in an organ of a patient using many electrodes (for example, diagnostic catheters may include as many as 48 or more electrodes to yield increased resolution electroanatomical maps).

Electro-anatomical (EA) mapping of an organ, such as a heart, may comprise (i) moving a distal tip of a catheter within the inner volume of the heart, (ii) acquiring electro-physiological (EP) signals on surfaces of the heart, and (iii) presenting the signals to a user, e.g., over a three-dimensional (3D) map of the catheter and the heart.

In some cases, a physician performing the EA mapping may use one or more catheters having a large number of electrodes, such as the Biosense Webster's OctaRay® or OPTRELL® catheters having, each, about forty-eight mapping electrodes. Using such catheter may result in acquisition of an overwhelming number of signals and data for the user to interpret during the EA mapping procedure. More specifically, (i) the user has to capture and analyze a lot of data in real time, (ii) the signals presented to the user are not correlated to their location over the catheter, and (iii) adjusting and/or filtering specific signals is time consuming.

In some examples, a system for displaying such multi-electrode catheters (e.g., OctaRay® or OPTRELL® catheters), and signals acquired by the catheter electrodes over time comprises: an interface, a processor, and a display device, also referred to herein as a display, for brevity.

In some examples, the interface is configured to receive, from at least first and second electrodes, among the electrodes of the catheter, first and second signals, respectively, which are acquired in the heart by the first and second electrodes during a time interval.

In some examples, the processor is configured to produce a three-dimensional (3D) representation of (i) at least a portion of the catheter comprising at least the first and second electrodes, and (ii) first and second traces corresponding to the first and second signals.

In the present example, the first and second traces are displayed, on the display device, in a 3D space relative to physical positions of the first and second electrodes on the catheter, respectively.

In some examples, the electrodes are coupled to splines of the catheter, for example, the OPTRELL® catheter has about six splines, and about eight electrodes coupled to each spline. Moreover, the first and second traces that are corresponding to the first and second signals, are displayed on respective time axes that, in the present example, are orthogonal to the first and second electrodes, respectively.

In some examples, the processor is configured to also display, in the 3D representation, at least a portion of the splines, and to rotate the 3D representation in response to instructions received from a user (e.g., a physician who wishes to see the electrodes and/or traces from a different orientation). Moreover, the processor is configured to display a plurality of selectable elements corresponding to at least one of (i) the one or more splines of the catheter, and (ii) at least the first and second electrodes. In case the user selects one or more of the of selectable elements, the processor is configured to toggle the display of the traces (and optionally the splines and/or electrodes) corresponding to the selectable elements in the 3D representation. Example implementations of all these techniques are described in detail in FIGS. 2 and 3 below.

In some examples, the system may provide the user with both the 3D representation described above, and a two-dimensional display of electrocardiogram (ECG) signals known in the art. In such examples, in response to selecting or deselecting a spline or an individual electrode in the 3D representation, the processor is configured to activate or deactivate, respectively, the display of the traces in the 3D representation, and optionally, also in the 2D display of the ECG signals. In other words, the user may turn on and off selected signals in the 3D representation and/or in the 2D display of the ECG signals, at the same time.

The disclosed techniques provide the user with a customized presentation of any desired combination of splines, electrodes, and signals of interest, and thereby, allow the user to focus on the features of interest while analyzing a large number of signals acquired in an organ of a patient.

System Description

FIG. 1 is a schematic, pictorial illustration of a catheter-based electrophysiology mapping and ablation system 10, in accordance with an example of the present disclosure.

In some examples, system 10 includes multiple catheters, which are percutaneously inserted by a physician 24 through the patient's vascular system into a chamber or vascular structure of a heart 12. Typically, a delivery sheath catheter is inserted into the left or right atrium near a desired location in heart 12. Thereafter, one or more catheters can be inserted into the delivery sheath catheter so as to arrive at the desired location within heart 12. The plurality of catheters may include catheters dedicated for sensing Intracardiac Electrogram (IEGM) signals, catheters dedicated for ablating and/or catheters adapted to carry out both sensing and ablating. An example catheter 14 that is configured for sensing IEGM is illustrated herein. In some embodiments, physician 24 may place a distal tip 28 of catheter 14 in close proximity with or in contact with tissue of the heart wall for sensing a target site in heart 12. Additionally, or alternatively, for ablation, physician 24 would similarly place a distal tip of an ablation catheter in contact with a target site for ablating tissue intended to be ablated.

Reference is now made to an inset 34 showing distal tip 28. In the present example, distal tip 28 of catheter 14 includes a representative (and non-limiting example) multi-spline and multi-electrode catheter, such as an OPTRELL® catheter having about six splines 22, each spline having about eight electrodes 26 distributed along the respective spline 22. Thus, distal tip 28 comprises about 48 electrodes 26 configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

Reference is now made back to the general view of FIG. 1. In some examples, magnetic based position sensor 29 may be operated together with a location pad 25 including a plurality of (e.g., three) magnetic coils 32 configured to generate a plurality of (e.g., three) magnetic fields in a predefined working volume. Real time position of distal tip 28 of catheter 14 may be tracked based on magnetic fields generated with location pad 25 and sensed by magnetic based position sensor 29. Details of the magnetic based position sensing technology are described, for example, in U.S. Pat. Nos. 5,391,199; 5,443,489; 5,558,091; 6,172,499; 6,239,724; 6,332,089; 6,484,118; 6,618,612; 6,690,963; 6,788,967; 6,892,091.

In some examples, system 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. This technique is also referred to herein as Advanced Current Location (ACL) and details of the impedance-based location tracking technology are described in U.S. Pat. Nos. 7,536,218; 7,756,576; 7,848,787; 7,869,865; and 8,456,182. In some embodiments, the magnetic based position sensing and the ACL may be applied concurrently, e.g., for improving the position sensing of one or more electrodes coupled to a shaft of a rigid catheter or to flexible arms or splines at the distal tip of another sort of catheter, such as the PentaRay® or OPTRELL® catheters, available from Biosense Webster, Inc., 31A Technology Drive, Irvine, CA 92618.

In some examples, a recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

In some examples, system 10 may include an ablation energy generator 50 that is adapted to conduct ablative energy to one or more of electrodes at a distal tip of a catheter configured for ablating tissue of heart 12. Energy produced by ablation energy generator 50 may include, but is not limited to, radiofrequency (RF) energy or pulse trains of pulsed-field ablation (PFA) energy, including monopolar or bipolar high-voltage DC pulses as may be used to effect irreversible electroporation (IRE), or combinations thereof. In the present example, catheter 14 does not include an ablation electrode, but as described above, system 10 may comprise an ablation catheter (no shown) configured to apply the RF energy and/or the pulse trains of PFA energy to tissue of the wall of heart 12.

In some examples, patient interface unit (PIU) 30 is an interface configured to establish electrical communication between catheters, electrophysiological equipment, power supply and a workstation 55 for controlling the operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

In some examples, workstation 55 includes a storage device, a processor 77 with suitable random-access memory, or storage with appropriate operating software stored therein, an interface 56 configured to exchange signals of data (e.g., between processor 77 and another entity of system 10) and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (4) displaying on display device 27 sites of interest such as places where ablation energy has been applied or intended to be applied. In some examples, processor 77 is configured to receive position signals from at least one of position sensor 29 and the ACL. Based on the position signals, processor 77 is configured to track the position of distal tip 28, and to display the position of distal tip 28 over map 20. One commercial product embodying elements of the system 10 is available as the CARTO™ 3 System, available from Biosense Webster, Inc., 31A Technology Drive, Irvine, CA 92618.

Reference is now made to an inset 31 showing an example of electrograms 21 displayed over display device 27. In some examples, processor 77 is configured to display electrograms using any suitable configuration. In the example of inset 31, processor 77 presents about six sets 35a, 35b, 35c, 35d, 35e and 35f of electrograms 21, each set has about seven electrograms 21 of bipolar signals sensed between seven respective pairs of adjacent electrodes 26 of a respective spline 22. For example, set 35a comprises (i) a first electrogram 21 represents a bipolar signal measured between the first and second electrodes 26 of a given spline 22, and (ii) six more electrograms 21 representing signals measured between the other pairs of adjacent electrodes along the same given spline 22. In this example, the seventh electrogram 21 represents a bipolar signal measured between the seventh and eighth electrodes 26, which is the last pair of electrodes 26 located along the same given spline 22.

When heart 12 beats, electrophysiological (EP) waves are propagating along sections of the heart 12 for setting the pace of the heart beats. In some examples, processor 77 is configured to display over each electrogram 21, an annotation 36 indicative of the time in which a propagating EP wave was sensed by a bipolar signal sensed between a respective pair of electrodes 26.

In the example shown in inset 31, processor 77 presents to physician 24 about 42 electrograms 21 and about 42 respective annotations 36, which may be an overwhelming amount of data for physician 24 to interpret in order to identify one or more regions and/or sources of arrhythmia in heart 12. More generally, a large number of electrogram traces and annotations may be displayed to physician 24 using a different presentation that may improve the ability of physician 24 (and other users of system 10) to manipulate and interpret the large amount of data collected by approximately the electrodes of distal tip 28. Examples of the present disclosure that are depicted in FIGS. 2, 3 and 4 below, provide users of system 10 with improved techniques for visualizing and analyzing the data (e.g., a large number of electrogram traces and annotations), and thereby, may assist the users in improving the interpretation of the data.

Displaying Traces of Signals Over a 3D Map of a
Multi-Electrode Catheter

FIG. 2 is a schematic, pictorial illustration of a 3D map 40 presenting distal tip 28 and traces 33, in accordance with an example of the present disclosure. In some examples, processor 77 is configured to present map 40 instead of map 20 shown in FIG. 1 above, so that both map 40 and electrograms 21 (of FIG. 1 above) are presented on display device 27 at the same time. In other examples, map 40 may replace electrograms 21 shown in inset 31 of FIG. 1 above.

In the example of FIG. 2, traces 33 correspond to electrogram signals (also referred to herein as signals, for brevity) acquired over time by electrodes 26. In the example of FIG. 1 above the signals comprise bipolar signals presented as electrograms 21, whereas in the example of FIG. 2, the signals may comprise (i) unipolar signals acquired between electrode 26 and reference electrodes (e.g., body surface ECG electrodes 18), or (ii) bipolar signal acquired between any suitable pair of electrodes 26 of distal tip 28. Note that the techniques described below in FIGS. 2 and 3 are applicable for both unipolar and bipolar signals.

In some examples, interface 56 is configured to receive from some of electrodes 26 or from each electrode 26, a signal acquired in heart 12 during a time interval 44 shown in map 40 along a time axis t, which is typically orthogonal to the respective electrodes 26. More specifically, during time interval 44, interface 56 may receive at least first and second signals from at least electrodes 26a and 26b, respectively.

In some examples, processor 77 is configured to produce map 40, which is a 3D representation of at least a portion of distal tip 28 comprising at least electrodes 26a and 26b, and optionally selected splines 22 of distal tip 28. In the example of FIG. 2, map 40 comprises all splines 22 and electrodes 26 of distal tip 28, and processor 77 is configured to present multiple traces 33 including at least traces 33a and 33b (also referred to herein as first and second traces) corresponding to the first and second signals, respectively. Note that traces 33 are displayed, on display device 27, in a 3D space relative to the physical positions of the respective electrodes 26 that acquired the signals. More specifically, traces 33a and 33b are displayed in the 3D space of map 40 relative to the respective physical positions of electrodes 26a and 26b on splines 22 of distal tip 28.

In some examples, processor 77 is configured to display in map 40 a plurality of selectable elements 41 and 42 corresponding to the selection and deselection of splines 22 and electrodes 26 of distal tip 28, respectively. More specifically, map 40 comprises (i) selectable elements 41 for selecting and deselecting columns of electrodes 26 distributed along respective splines 22, and (ii) selectable elements 42 for selecting and deselecting rows of electrodes 26 distributed across splines 22. For example, physician 24 may activate a selectable element 41a for selecting electrodes 26 distributed along a spline 22a, and may deactivate a selectable element 41b for deselecting electrodes 26 distributed along a spline 22b. Similarly, physician 24 may activate a selectable element 42b for selecting electrode 26b (even though spline 22b has been deselected as described above), and may deactivate a selectable element 42a for deselecting electrode 26c.

In some examples, based on the selection carried out by physician 24, processor 77 is configured to toggle the display of traces 33 corresponding to the splines and/or electrodes selected by physician 24. For example, traces 33a and 33b that correspond to the signals received from electrodes 26a and 26b, respectively, are presented in map 40, whereas in response to the deselection of electrode 26c, processor 77 does not present the corresponding trace 33 in map 40. Moreover, processor 77 is configured to present annotations 36 over at least some of the selected traces 33.

In the present example, annotations 36 are falling along a virtual vector 37. In some examples, based on the presentation of annotations 36 and virtual vector 37, processor 77 is configured to present, e.g., over the map of distal tip 28, a vector 39, which is approximately parallel to virtual vector 37, and is indicative of the propagation direction of the EP wave relative to splines 22 and electrodes 26 of distal tip 28.

In some examples, based on the position and orientation of distal tip 28 (obtained using the position signals described in FIG. 1 above), processor 77 is configured to display over map 20 of heart 12 (shown in FIG. 1 above), tags indicative of vector 39. Additionally, or alternatively, processor 77 may present maps 20 and 40 overlayed on one another, so as to correlate between the position and orientation of vector 39 and the position of distal tip 28 in heart 12.

FIG. 3 is a schematic, pictorial illustration of a 3D map 60 presenting distal tip 28 and traces 33, in accordance with another example of the present disclosure. Map 60 may replace, for example, at least one of map 40 of FIG. 2 above, map 20 of FIG. 1 above, and electrograms 21 shown in inset 31 of FIG. 1 above.

In the context of the present disclosure and in the claims, map 20 (of FIG. 1), map 40 (of FIG. 2) and map 60 (of FIG. 3) are also referred to herein as 3D representations of at least one of traces 33, electrodes 26 and splines 22.

In some examples, in response to instructions received from physician 24 (or any other user), processor 77 is configured to rotate the 3D representation that may comprise at least a portion of splines 22, electrodes 26, and optionally the corresponding traces 33 and annotations 36. For example, physician 24 may use a suitable input device, such as a mouse, a track ball, or key(s) of a keyboard, for rotating distal tip 28 and corresponding traces 33 and annotations 36, so as to see specific electrodes 26, traces 33 and annotations 36 from a different orientation (e.g., compared to that shown in FIG. 2 above). The rotation may be carried out in a direction 46 about a longitudinal axis 45, in a direction 48 about a latitudinal axis 47, and in a combination of directions 46 and 48.

Additionally, or alternatively, in response to instructions received from physician 24 (or any other user), processor 77 is configured to perform various operations, such as but not limited to: (i) displaying a selected section of one or more traces 33 (e.g., using a check box), (ii) adjusting the amplitude of a selected trace 33, (iii) and performing zoom-in and/or zoom-out on specific portions of distal tip 28 and traces 33, and (iv) removing and/or adjusting the position of selected annotations 36. For example, physician 2 may adjust the amplitude of the signal received from at least one of electrodes 26, and responsively, processor 77 is configured to adjust the amplitude of at least one of traces 33 corresponding to the adjusted signal(s).

In some examples, processor 77 is configured to display, at the same time, (i) the 3D representation (e.g., map 40 or map 60), and (ii) a 2D display of electrogram signals, such as the display of electrograms 21 shown in inset 31 of FIG. 1 above. In such examples, in response to physician 24 selecting or deselecting a spline 22 or an individual electrode 26 in the 3D representation, processor 77 is configured to activate or deactivate, respectively, the display of the respective traces 33 in the 3D representation (as described in FIG. 2 above), and optionally, also in the 2D display of electrograms 21 of FIG. 1 above. In other words, physician 24 may turn on and off selected: (i) traces 33 in the 3D representation, and (ii) electrograms 21 in the 2D display, at the same time.

FIG. 4 is a flow chart that schematically illustrates a method for displaying at least a portion of distal tip 28 and traces 33 indicative of the signals acquired by corresponding electrodes 26 over time interval 44, in accordance with an example of the present disclosure.

The method begins at a signal receiving step 100 with processor 77 receiving from electrodes 26 signals acquired during time interval 44, as described in detail in FIG. 2 above.

At a 3D-view production step 102, processor 77 produces map 40 comprising a 3D representation of at least a portion of distal tip 28 having at least electrodes 26a and 26b, and at least traces 33a and 33b corresponding to the signals received from electrodes 26a and 26b, respectively, as described in detail in FIG. 2 above.

At a displaying step 104 that concludes the method, processor 77 displays, e.g., over display device 27, at least traces 33a and 33b in a 3D space relative to the physical positions of at least electrodes 26a and 26b, respectively, as described in detail in FIG. 2 above.

In some examples, processor 77 is configured to display annotations 36 and vector 39, which is indicative of the propagation direction of the EP wave relative to splines 22 and electrodes 26 of distal tip 28, as shown and described in FIG. 2 above. Moreover, processor 77 is configured to display selectable elements 41 and 42 corresponding to the selection and deselection of splines 22 and electrodes 26 of distal tip 28, respectively, so that physician 24 may select or deselect which traces 33 s/he wants to view in map 40, as described in FIG. 2 above.

In some examples, in response to instructions received from physician 24, processor 77 may perform various operations, such as but not limited to: (i) displaying a selected section of one or more traces 33 (e.g., using a check box), (ii) adjusting the amplitude of a selected trace 33, (iii) and performing zoom-in and/or zoom-out on specific portions of distal tip 28 and traces 33, (iv) removing and/or adjusting the position of selected annotations 36, and (v) three-dimensional rotating the 3D representation of distal tip 28, traces 33 and annotations 36, as described in detail in FIG. 3 above.

Although the examples described herein mainly address techniques for dynamically altering the transparency level of sub-volumes in patient heart during an electrophysiological (EP) procedure. The methods and systems described herein can also be used in other applications, such as in dynamically displaying inner volumes or surfaces in any other suitable organs of a patient.

Example 1

A system (10) includes an interface (56) and a processor (77). The interface is configured to receive, from at least first and second electrodes (26a, 26b) of a catheter (14), first and second signals, respectively, which are acquired over at least a time interval (44) by the at least first and second electrodes at an organ (12) of a patient (23). The processor is configured to produce a three-dimensional (3D) representation (40) of at least a portion of the catheter and first and second traces (33a, 33b) corresponding to the first and second signals, wherein the first and second traces are displayed in a 3D space relative to physical positions of the first and second electrodes (26a, 26b) on the catheter, respectively.

Example 2

The system according to Example 1, wherein the first and second traces corresponding to the first and second signals are displayed on respective time axes orthogonal to the first and second electrodes, respectively.

Example 3

The system according to any of Examples 1 and 2, wherein the processor is configured to display, in the 3D representation, one or more splines of the catheter comprising at least the first and second electrodes.

Example 4

The system according to Example 3, wherein the processor is configured to rotate the 3D representation in response to instructions received from a user.

Example 5

The system according to Example 3, wherein the processor is configured to display a plurality of selectable elements corresponding to at least one of (i) the one or more splines, and (ii) the first and second electrodes; and in response to a selection by the user of one or more of the plurality of selectable elements, the processor is configured to toggle the display of at least one of: (i) the one or more splines, and (ii) the first and second electrodes corresponding to the selectable elements in the 3D representation.

Example 6

The system according to Example 5, wherein, in response to the selection by the user, the processor is configured to toggle the display of at least one of the first and second traces responsively to toggling the display of at least one of the first and second electrodes, respectively.

Example 7

The system according to Example 6, wherein the processor is configured to produce a two-dimensional (2D) representation of at least first and second electrograms indicative of at least the first and second signals, and wherein, in response to the selection by the user, the processor is configured to toggle the display of at least one of the first and second electrograms responsively to toggling the display of at least one of the first and second traces, respectively.

Example 8

The system according to any of Examples 1 and 2, wherein the time interval comprises first and second times in which an electrophysiological (EP) wave propagates across the tissue and sensed by the first and second electrodes, respectively, and wherein the processor is configured to display, over the first and second traces, at least first and second annotation, which are indicative of first and second times, respectively.

Example 9

The system according to Example 8, wherein, based on at least the first and second annotations, the processor is configured display over the 3D presentation, a vector indicative of a direction of the EP waves propagating across the tissue between at least the first and second electrodes.

Example 10

The system according to Example 1, wherein, in response to receiving an adjustment of a signal amplitude of at least one of the first and second signals, the processor is configured to adjust a trace amplitude of at least one of the first and second traces, respectively.

Example 11

A method, including:
receiving, from at least first and second electrodes (26*a*, 26*b*) of a catheter (14), first and second signals, respectively, which are acquired over at least a time interval (44) by the at least first and second electrodes at an organ (12) of a patient (23);
producing a three-dimensional (3D) representation (40) of at least a portion of the catheter and first and second traces (33*a*, 33*b*) corresponding to the first and second signals; and
displaying the first and second traces (33*a*, 33*b*) in a 3D space relative to physical positions of the first and second electrodes (26*a*, 26*b*) on the catheter, respectively.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. A system, comprising:
an interface, which is configured to receive, from at least first and second electrodes of a catheter, first and second signals, respectively, which are acquired over at least a time interval by the at least first and second electrodes from a tissue at an organ of a patient, wherein the electrodes are located along one or more splines of the catheter; and
a processor configured to produce a three-dimensional (3D) representation of at least a portion of the catheter and first and second traces corresponding to the first and second signals, wherein the first and second traces are displayed in a 3D space relative to physical positions of the first and second electrodes on the catheter, respectively,
wherein the processor is configured to display, in the 3D representation, the one or more splines of the catheter comprising the at least the first and second electrodes,
wherein the processor is configured to display a plurality of selectable elements corresponding to at least one of (i) the one or more splines, and (ii) the first and second electrodes; and in response to a selection by the user of one or more of the plurality of selectable elements, the processor is configured to toggle the display of at least one of: (i) the one or more splines, and (ii) the first and second electrodes corresponding to the selectable elements in the 3D representation, and
wherein the processor is further configured to toggle the display of at least one of the first and second traces responsively to toggling the display of at least one of the first and second electrodes, respectively.

2. The system according to claim 1, wherein the first and second traces are displayed along first and second time axes respective to the first and second signals, the first time axis extending orthogonally to the spline comprising the first electrode, and the second time axis extending orthogonally to the spline comprising the second electrode.

3. The system according to claim 1, wherein the processor is configured to rotate the 3D representation in response to instructions received from a user.

4. The system according to claim 1, wherein the processor is configured to produce a two-dimensional (2D) representation of at least first and second electrograms indicative of at least the first and second signals, and wherein, in response to the selection by the user, the processor is configured to toggle the display of at least one of the first and second electrograms responsively to toggling the display of at least one of the first and second traces, respectively.

5. The system according to claim 1, wherein the time interval comprises first and second times in which an electrophysiological (EP) wave propagates across the tissue and sensed by the at least first and second electrodes, respectively, and wherein the processor is configured to display, over the first and second traces, at least first and second annotations, which are indicative of first and second times, respectively.

6. The system according to claim 5, wherein, based on at least the first and second annotations, the processor is configured display over the 3D presentation, a vector indicative of a direction of the EP waves propagating across the tissue between at least the first and second electrodes.

7. The system according to claim 1, wherein, in response to receiving an adjustment of a signal amplitude of at least one of the first and second signals, the processor is configured to adjust an amplitude of at least one of the first and second traces, respectively.

8. A method, comprising:
receiving, from at least first and second electrodes of a catheter, first and second signals, respectively, which are acquired over at least a time interval by the at least first and second electrodes from a tissue at an organ of a patient, wherein the electrodes are located along one or more splines of the catheter;

producing a three-dimensional (3D) representation of at least a portion of the catheter and first and second traces corresponding to the first and second signals;

displaying, in the 3D representation, the one or more splines of the catheter comprising the at least the first and second electrodes, displaying the first and second traces in a 3D space relative to physical positions of the first and second electrodes, respectively, displaying a plurality of selectable elements corresponding to at least one of (i) the one or more splines, and (ii) the first and second electrodes; and in response to a selection by the user of one or more of the plurality of selectable elements, the processor is configured to toggle the display of at least one of: (i) the one or more splines, and (ii) the first and second electrodes corresponding to the selectable elements in the 3D representation, and toggling the display of at least one of the first and second traces responsively to toggling the display of at least one of the first and second electrodes, respectively.

9. The method according to claim 1, wherein displaying the first and second traces comprises displaying the first and second traces along first and second time axes respective to the first and second signals, the first time axis extending orthogonally to the spline comprising the first electrode, and the second time axis extending orthogonally to the spline comprising the second electrode.

10. The method according to claim 8, wherein displaying the first and second traces comprises rotating the 3D representation in response to instructions received from a user.

11. The method according to claim 8, and comprising producing a two-dimensional (2D) representation of at least first and second electrograms indicative of at least the first and second signals, and wherein, in response to the selection by the user, toggling the display of at least one of the first and second electrograms responsively to toggling the display of at least one of the first and second traces, respectively.

12. The method according to claim 8, wherein the time interval comprises first and second times in which an electrophysiological (EP) wave propagates across the tissue and sensed by the first and second electrodes, respectively, and comprising displaying, over the first and second traces, at least first and second annotations, which are indicative of first and second times, respectively.

13. The method according to claim 12, and comprising, based on at least the first and second annotations, displaying over the 3D presentation, a vector indicative of a direction of the EP waves propagating across the tissue between at least the first and second electrodes.

14. The method according to claim 8, wherein displaying the first and second traces comprises, in response to receiving an adjustment of a signal amplitude of at least one of the first and second signals, adjusting a trace amplitude of at least one of the first and second traces, respectively.

* * * * *